United States Patent [19]
Sonek et al.

[11] Patent Number: 5,631,141
[45] Date of Patent: May 20, 1997

[54] HIGH RESOLUTION BIOSENSOR FOR IN-SITU MICROTHERMOMETRY

[75] Inventors: Gregory J. Sonek; Yagang Liu; Bruce J. Tromberg, all of Irvine; Michael W. Berns, Canyon, all of Calif.

[73] Assignee: The Regents of the University of California, Oakland, Calif.

[21] Appl. No.: 435,354

[22] Filed: May 5, 1995

[51] Int. Cl.⁶ .................................................. C12Q 1/02
[52] U.S. Cl. ........................... 435/29; 435/968; 436/172
[58] Field of Search ........................ 435/29, 817, 968; 436/172; 422/82.07

[56] References Cited

U.S. PATENT DOCUMENTS

| | | | |
|---|---|---|---|
| 5,094,819 | 3/1992 | Yager et al. | 422/82.07 |
| 5,366,881 | 11/1994 | Singh et al. | 435/177 |

FOREIGN PATENT DOCUMENTS 0252578  1/1988  European Pat. Off. .

OTHER PUBLICATIONS

Epand, R., Hexagonal Phase Forming Propensity Detected in Phosphilipid Bilayers with Fluorescent Probes, Biochemistry 1992 31, 1550–1554.

Abrams, S., Use of a Visible Fluorescence Dye in a Fiberoptic Sensor to Detect General Anesthetics, Proceedings of Advances in Fluorescence Sensing Technology vol. 1885, pp. 62–71 1993.

Primary Examiner—Ralph Gitomer
Attorney, Agent, or Firm—Allston L. Jones

[57] ABSTRACT

The present invention comprises a method for use of a biosensor for in-situ microthermometry. This biosensor is a substantially spherical vesicle impregnated with a dopant which varies its optical emission spectrum as a function of the local environmental temperature of the biosensor in the temperature range to be observed. In the preferred embodiment of the present invention, this dopant is the fluorescent dye 6-dodecanoyl-2-dimethylamino-naphthalene (Laurdan™). This method for in-situ measurement of temperature in a biological system uses such a vesicle by introduction of the vesicle into the biological system to be measured and manipulation of the vesicle to the location where temperature is to be measured. The temperature is then calculated from the optically measured generalized polarization at that location and the known relationship between temperature and generalized polarization for the membrane of the vesicle.

8 Claims, 5 Drawing Sheets

HIGH RESOLUTION BIOSENSOR FOR IN-SITU MICROTHERMOMETRY

GOVERNMENT RIGHTS

This invention was made with Government support under Grant (Contract) No. BIR-9121325 awarded by the National Science Foundation. The Government has certain rights in this invention.

FIELD OF THE INVENTION

The present invention relates to in-situ microthermometry, and more particularly to a high resolution biosensor adapted for in-situ microthermometry.

BACKGROUND OF THE INVENTION

With the advent of modern study and treatment of biological systems, there has arisen an increasing need for monitoring of the internal state of biological systems that is either non-invasive or is minimally invasive. For example, micro-endoscopes and catheter-based ultrasound probes have been developed to produce images of the interior of organisms. Many other technologies have been developed to measure the physiological and anatomical features of the biological system in question. These technologies have proven invaluable in the diagnosis and treatment of such systems.

It is desirable, therefore, to perform thermal imaging of biological systems in a minimally invasive manner as well. Such imaging would make possible real-time three-dimensional thermal mapping, allowing both researchers and medical personnel to study the micro-metabolic functioning of cell and tissue systems in-situ, i.e., in actually functioning biological systems. Such imaging could provide to such personnel otherwise presently unavailable information about the actual metabolic functioning of the biological system in question.

In addition, such thermal mapping could prove invaluable in assessing in real-time the effects of sample exposure to a highly focused laser beam during both diagnostic and therapeutic treatment. Given the increasing reliance on the use of such lasers in both diagnostic and therapeutic treatment, such imaging could become an important method of critically assessing the ongoing treatment and for avoiding unintended thermal damage to the tissue.

Further, such monitoring may facilitate the development of new thermal techniques for the diagnosis and treatment of the tissues in question. For example, temperature-sensitive liposomes have been used in combination with the inducement of local hyperthermia or hypothermia (see for example, M. B. Yatvin, I. M. Tegmo-Larsson and W. H. Dennis, "Temperature and pH-Sensitive Liposomes for Drug Targeting", *Methods in Enzymology*, Vol. 149 (1987), pp. 77-87). The availability of in-situ thermal monitoring will undoubtedly lead to additional diagnostic and therapeutic treatment that cannot yet be foreseen.

In addition, there are a wide range of systems other than biological systems for which; microthermometry would be advantageous. For example, it may be desirable to measure temperatures in-situ in a variety of fluidic media, such as water, gasoline, and solvents. Again, the availability of such imaging would clearly be advantageous in additional ways yet unforeseen.

There have therefore been a number of attempts to provide techniques for the measurement of temperature, temperature changes and heating effects in dielectric and organic samples. Such techniques previously attempted include laser-induced fluorescence, Raman spectroscopy, photochemical absorption spectroscopy, and Zeeman interferometry. These techniques have proven either to be limited by poor spatial, temporal, or thermal resolution, or are difficult to adapt to in-situ use in biological or other systems.

Hence, it would be advantageous to develop a high resolution sensor designed for use in-situ in biological systems. Such a sensor should ideally be organically compatible with the surrounding tissue to avoid reactions therewith which would be both disruptive of the accurate measurement of temperature and normal metabolic function as well as potentially damaging to the tissue being observed. Such a sensor should additionally be easily manipulated using conventional technology.

SUMMARY OF THE INVENTION

The present invention comprises a biosensor for in-situ microthermometry. This biosensor is constructed in the form of a substantially spherical vesicle. The vesicle has at least one phospholipid layer, yet may have a membrane that includes a plurality of organic phospholipid bilayers, i.e., is multilamellar. The membrane is impregnated with a dopant that varies its optical emission spectrum as a function of the local environmental temperature of the biosensor in the temperature range to be observed, i.e., those compatible with the functioning of the biological system. In the preferred embodiment of the present invention, this dopant is a fluorescent dye, and preferably 6-dodecanoyl-2-dimethylamino-naphthalene, which is known as Laurdan™.

The present invention also comprises a method for in-situ measurement of temperature in a biological system. First, a vesicle as described above is chosen with specific properties appropriate to the system whose temperature is to be measured. More specifically, the vesicle is chosen such that the temperature at which the membrane undergoes a phase transition between gel and liquid-crystalline states is either below the range of temperatures to be measured, if heating is anticipated, or above the range of temperatures to be measured, if cooling is anticipated. Ideally, a calibration generalized polarization for the vesicle is then determined by measuring the generalized polarization of the vesicle at a predetermined temperature. The generalized polarization is the ratio (IG−IL)/(IG+IL) of the difference to the sums of the intensities measured at the maximum emission wavelengths in the gel (IG) and liquid-crystalline (IL) phases of the phospholipid.

Next, the biosensor is introduced into the biological system to be measured, and manipulated to the location where temperature is to be measured. This manipulation can be performed by optical laser traps, also known as "optical tweezers", or by attachment to optical fibers. To obtain the temperature measurements, the generalized polarization of the vesicle at that location is optically measured, and the value for the temperature is calculated from the calibration generalized polarization and the known relationship between temperature and generalized polarization for the membrane of the vesicle.

DESCRIPTION OF THE PREFERRED EMBODIMENT

The present invention includes an optical biosensor for measurement of temperature with extremely high spatial and thermal resolution. It is organically-based, compatible with other biological materials, and can be fabricated to dimensions that can provide submicron spatial resolution. It is effectively an optically-based sensor that in essence "up-converts" thermal radiation into visible optical radiation that can be detected using conventional methods, such as fluorescence spectroscopy. Such a biosensor is of a small size and can exist in a fluidic media, such as water, gasoline, and solvents. It can be manipulated by a number of methods, such as a focused laser beam or optical laser trap (also known as "optical tweezers") or by attachment to an optical fiber. The latter method creates a fiber-optic microthermometric probe, and is well-adapted for use in conventional laser catheters.

Figure 1:
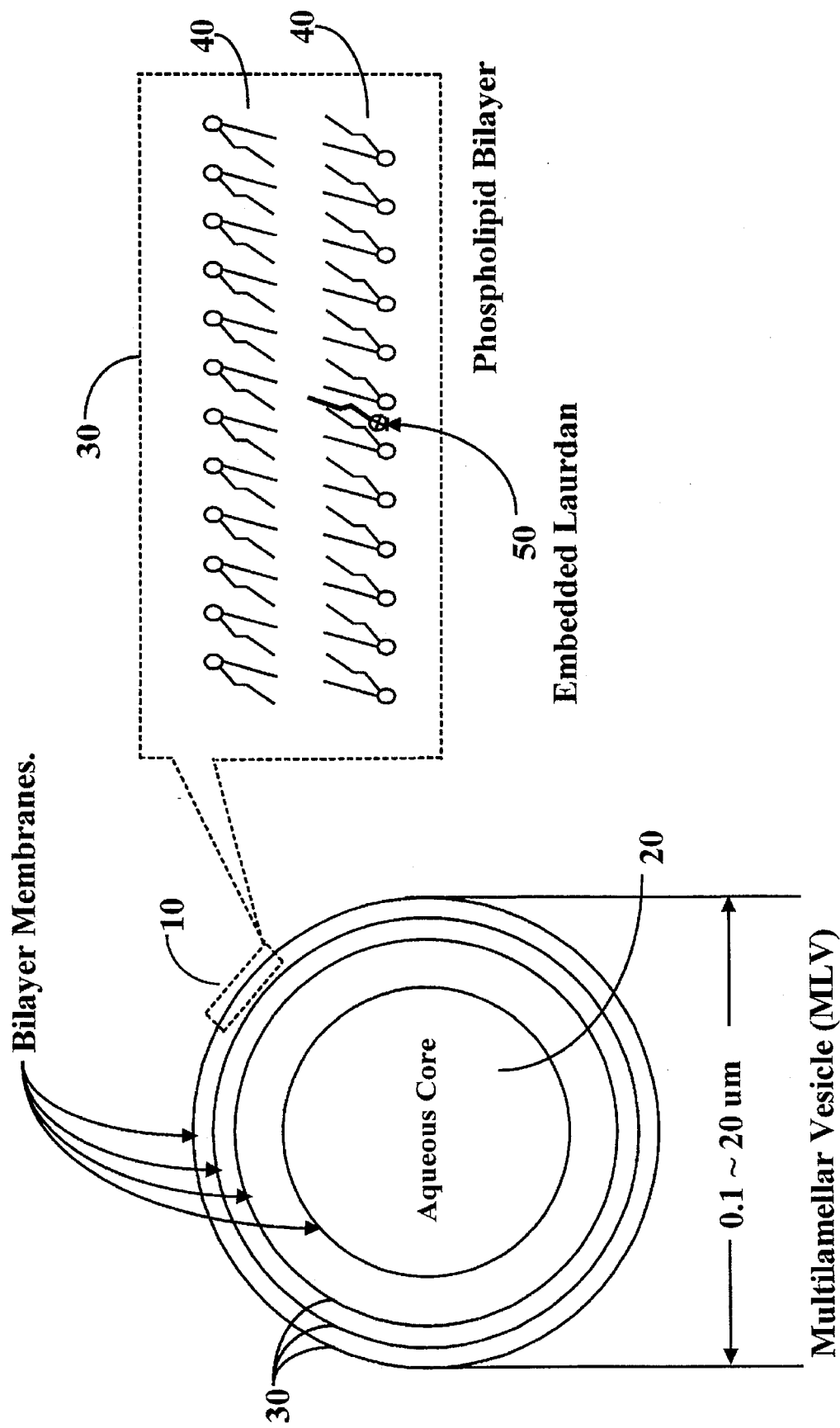
FIG. 1 is a cross-sectional representation of an exemplary phospholipid vesicle according to the present invention.

FIG. 1 illustrates a typical microspherical sensor 10 according to the present invention. One or more bilayer membranes 30 surround an aqueous core 20. Each bilayer membrane 30 comprise two layers of phospholipids 40. Embedded within the membrane layers are the dopant molecules 50. However, while the illustrated sensor 10 shown has a plurality of bilayer membranes 30, the sensor may be constructed with only a single membrane 30, and even with a single bilayer in the membrane (although multiple bilayers provide an improved ease of manufacture and stability of the structure). Such vesicles, without the dopant, are known to those skilled in the art.

It should also be noted that the aqueous core 20 may contain any of a number of fluids appropriate to the environment into which the sensor 10 is to be deployed.

Such a vesicle, without the dopant, can be manufactured through methods known to those skilled in the art. In one of the preferred embodiments of the invention, a phospholipid liposome such as 15-OPC(1,2-diacylpentadecanoyl-glycero-phosphocholine) manufactured by Avanti Polar Lipids of Alabaster, Ala., may be mixed with the dye probe Laurdan™ (6-dodecanoyl-2-dimethylamino-naphthalene) manufactured by Molecular Probes of Eugene, Oreg., in molar ratios of between 100:1 and 1000:1, in a 200 ml flask containing a chloroform solution. The solution is then dried in a rotary evaporator under vacuum. Subsequently, the water-saturated solution is passed through the flask for 20 minutes.

To produce large unilamellar vesicles, the dried lipids are first immersed in a 0.2M sucrose solution for 2 hours at 47° C., and then centrifuged at 12,000 g for 10 minutes.

To produce multilamellar vesicles, the dried lipid samples are resuspended in a phosphate buffered saline solution (PBS), manufactured by Sigma of St. Louis, Mo. (Cat. No. D1408). Next the mixture is heated to 55° C., and then vortexed.

The unilamellar and multilamellar structures of the vesicle membranes have been confirmed experimentally for test samples. Because the Laurdan™ dopant is an amphiphilic molecule, it is automatically incorporated into the membrane of the vesicle during the phospholipid molecule aggregation process, creating a structure as shown in FIG. 1. Substantially spherical Laurdan™-impregnated vesicles have been manufactured that could vary in size from 0.1 to 20 µm in diameter.

It should be obvious to those skilled in the art that while the above combination provides a particularly advantageous sensor response, a variety of phospholipids and dopants may be used. For example, the membrane 30 may be manufactured from DPPC (dipalmitoyl-phosphatidyl choline), DMPC (dimyristoyl phosphocholine), or other phospholipids known in the art.

The operation of the sensor 10 may be understood as follows. First, it must be noted that phospholipid membranes 30 undergo a phase transformation between a gel state and a liquid crystal state over a range centered at a temperature called the "transition temperature", $T_r$, with the bilayer having a mixed state over the transition range. This transition changes the membrane's permeability to water, and is an important part of the membrane's behavior.

Next, it must be understood that the dopant 50, in the preferred embodiment Laurdan™, undergoes a large temperature-dependent shift in fluorescence because the dopant responds to the phase transition in the surrounding membrane 30. To quantify this behavior, an intensity contrast ratio called "generalized polarization" is determined for the sensor 10. Generalized Polarization (GP) is defined as the ratio (IG−IL)/(IG+IL) of the difference to the sums of the intensities measured at the maximum emission wavelengths in the gel (IG) and liquid-crystalline (IL) phases.

Figure 2:
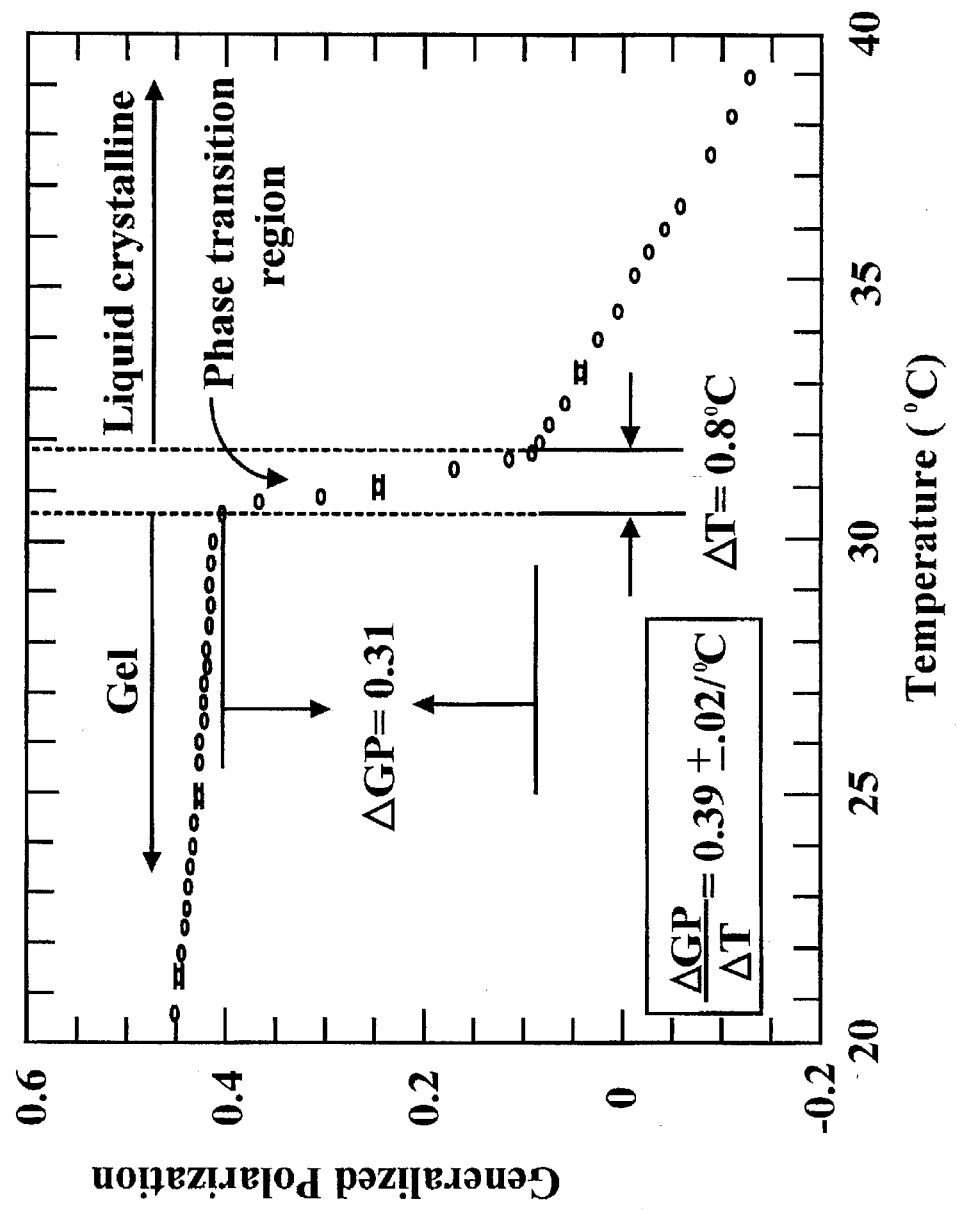
FIG. 2 is a graph of the response of the generalized polarization of an exemplary phospholipid vesicle according to the present invention and as described in Example 1 below.

The response of a typical sensor 10 is shown in FIG. 2, which is a plot of the GP of the sensor 10 as a function of the local temperature. At temperatures distant from the transition temperature, $T_r$, the slope of the curve is very shallow, and large temperature changes yield only small changes in GP. However, in a range of temperatures near the transition temperature corresponding to the phase transition of the membranes 30, the curve becomes very steep, and small changes in temperature correspond to large changes in GP. As a result, in this range, the sensor 10 provides high resolution thermometry.

For example, in a phospholipid bilayer membrane 30 consisting of phospholipid 15-OPC (1,2-diacylpentadecanoyl-glycero-phosphocholine), the phase transition temperature, $T_r$, is found to be 31° C., and the slope of the curve is very steep, $\Delta GP/\Delta T = 0.39 \pm 00.2/°C$. It should be noted that at the time of this invention $\Delta GP$ variations as small as 0.01 may be resolved. Hence, $\Delta T$ resolutions of 0.1° C. may be calculated. However, if the phospholipid bilayer membrane 30 is manufactured from DPPC and DMPC in a 1:1 ratio, then the transition temperature, $T_r$, is 38° C. and the $\Delta GP/\Delta T = 0.06$. Other choices of phospholipids and dopants will result in different transition temperatures and ratios $\Delta GP/\Delta T$.

EXAMPLE 1

The sensor 10 may be used for in-situ measurement of temperature in a biological system as illustrated in an example. In this example, the sensor is used to measure changes in tissue temperature induced by exposure of the tissue to focused laser radiation.

First, a sensor 10 is chosen with a transition temperature, $T_r$, appropriate for the sample to be measured. In this case, a sensor 10 is chosen which has a transition temperature, $T_r$, of 31° C. Hence, for this example, a 15-OPC membrane may be used, as described above.

The sensor 10 is initially at a temperature below the transition temperature, $T_t$, for example, 30.5° C., as the sample is expected to rise in temperature. If cooling were instead expected, it would be advantageous to start measurements at a temperature above $T_t$. This takes advantage of a wider portion of the sensitive temperature range of the sensor, which is centered about $T_t$.

The GP should be measured at a known or predetermined temperature to serve as a calibration for the sensor 10. Indeed, the whole GP to temperature response curve may be measured to calibrate the sensor.

Next, the sensor 10 is introduced into the biological system, and manipulated to the site whose temperature is to be measured, in this case the tissue exposed to the laser radiation. If the application were related to laser radiation used internal to a body as part of an optical fiber-based laser device, it could be advantageous to locate the biosensor on an optical fiber for ease of manipulation. Such a fiber may be located within the same catheter as the laser fiber-based device used for the procedure.

As the local temperature changes, it may be sampled by optically measuring the GP of the sensor 10. This is accomplished by observing the spectral characteristics of the sensor 10 and calculating the GP. Fluorescence may be measured with a high signal-to-noise ratio, resulting in the high resolution of GP noted above. Once the GP is known, the temperature may be computed since the relationship between GP and temperature is known and calibrated.

EXAMPLE 2

A similar example may be illustrated, which demonstrates the manner in which the measurements made be made. In this example vesicles with a OPC-15 membrane doped with Laurdan™ ($T_t$=31° C.) and an approximate size of 15 μm were used, as in Example 1, above.

Figure 3:
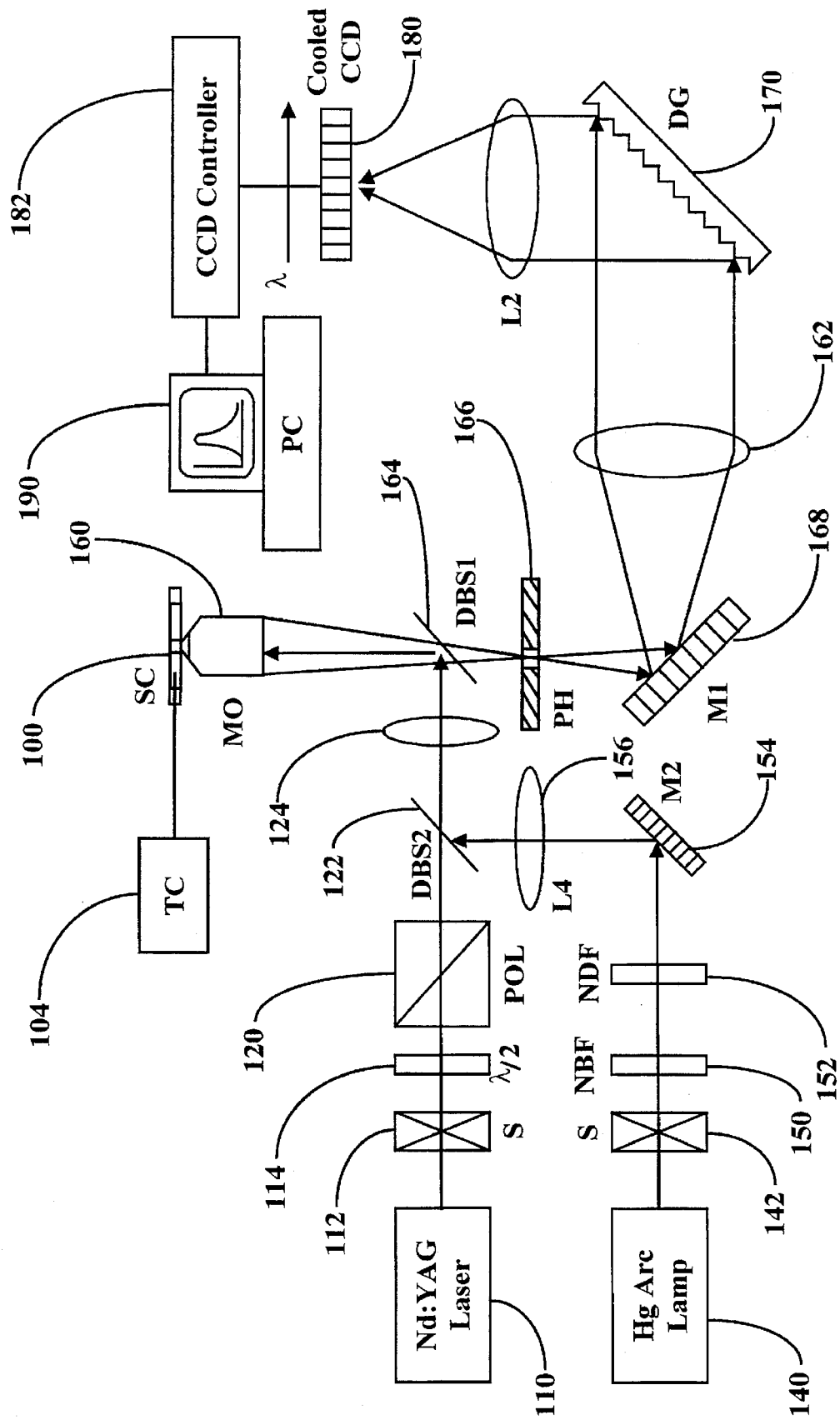
FIG. 3 is an system for measuring the fluorescence of a sensor according to the present invention while being subjected to a laser trapping beam.

An experimental system was developed for the simultaneous implementation of optical trapping and fluorescence spectroscopy, as illustrated in FIG. 3. An optical trapping beam was derived from a Nd:YAG laser 110. The laser used can emit a 1 Watt CW in the TEM$_{00}$ mode at a wavelength of 1.064 μm. Upon emerging from the laser, the polarization of the infrared (IR) beam was set using an IR polarizer 120. The beam was then directed into a high magnification (100×) and large (1.3 N.A.) oil immersion microscope objective 130. A 365-nm ultraviolet (UV) excitation beam was derived from a 200 W Hg arc lamp 140 used in conjunction with a narrow band filter 150, having a center wavelength of 365 nm and a bandwidth of 4 nm. This beam was made collinear with the trapping beam from laser 110, and then deflected into a focusing objective lens 160 via a UV/IR dichronic beam splitter 164.

An electronic shutter was used to control the fluorescence excitation time. A UV exposure time of 100 ms was used, and was found to be short enough to prevent photobleaching of the Laurdan™ dye.

The fluorescence emission from the optically trapped sample was collected by the same objective lens 160. It was then passed through an adjustable pinhole aperture 166 located at the image plane of the microscope objective. A pinhole aperture of 0.1–1 mm diameter effectively converts the optical system into a confocal trapping microscope with micron spatial resolution.

A 300 g/mm diffraction grating 170 was then used to disperse the light, which was subsequently focused onto an electrically cooled CCD array 180. Spectral data, collected over a 400 nm bandwidth, was acquired and analyzed using a 386DX/25 MHz NEC personal computer 190.

For sample sizes in the 2–20 μm size range, the detected fluorescence signal-to-noise ratio (S/N) for this system was found to exceed 1000 to 1.

The sample chamber itself was customized to contain a temperature control system and was capable of both containing the liposome suspensions, and for controlling the cell solution temperature. The chamber 100 consisted of two distinct microchambers (not shown in FIG. 3) placed on top of one another. The double microchamber design not only served to keep the cells sterile, but also maintained a stable sample temperature by minimizing the effects of fluid turbulence in the upper microchamber during the heating process. In the upper chamber, which was filled with de-ionized water, an electrically controlled heating coil was introduced to heat the fluid medium. This heat was conducted to the lower microchamber via a glass coverslip. A thermocouple was disposed within the lower microchamber to monitor the background solvent solution temperature. With a customized electronic feedback circuit, the chamber was designed to adjust and maintain a setpoint temperature while providing clear optical access for trapping, illumination, and fluorescence excitation beams.

After calibrating the laser power, sample temperatures could be measured. The general method of determining GP was first described by Parasassi et al. (*Biophysics Journal*, vol. 57, 1179–1186 (1990) and vol. 60, 179–189 (1991)), and is known to those skilled in the art. Specifically, the sample fluorescence was first measured at different sample temperatures and the peak emission was measured at each temperature. Since GP=(IG−IL)/(IG+IL), the and since IG and IL are each measured at maximum emission wavelengths, GP can be then calculated.

The gel state is formed at a temperature that is lower than that of the liquid-crystalline state. Thus, as the bilayer transitions between these two states with an increase in temperature, the sample fluorescence emission undergoes a red-shift, and the magnitude of GP decreases as IG and IL increases. Since this process is reversible, a decrease in sample temperature would correspond to a decrease in IL and increase in IG, with an increase in GP. For the phospholipid 15-OPC tagged with Laurdan™, the peak wavelengths corresponding to the pure gel and pure liquid-crystalline states are 440 nm (26° C.) and 490 nm (38° C.), respectively.

Given the possibility of dye photobleaching and UV-induced light stress, the intensity and duration of the UV excitation beam was carefully controlled.

The experiment consisted of bringing the vesicle into the field of view of the microscope, and exposing the cell to UV radiation, and measuring the GP. This was performed before and after switching on the laser trapping beam, and was measured for a range of time and incident laser power. Time-gated excitation was used to prevent photobleaching of the membrane probes. A UV power density of less than 100 mW/cm$^2$ and exposure time of 100 ms was used. Prior to optical trapping, the laser power and spot size were measured. For the cw Nd:YAG laser 110 used in this example, focused power levels were continuously varied from 0–500 mW. The focused spot size of the TEM$_{00}$ laser mode was determined to be approximately 0.80±0.15 μm at the sample plane using a scanning knife edged, when a 1.3 N.A. 100× microscope objective was used.

Prior to optical trapping, a GP plot was generated to serve as a calibration curve for sample temperature measurements.

By slowly increasing the temperature of the sample chamber by means of a heating coil embedded within the upper microchamber, a set of fluorescence emission spectra as a function of temperature from a freely suspended vesicle was acquired. This data was then converted into GP data. As described above, the temperature was then measured by increasing the temperature from a point below the transition temperature and measuring the fluorescence, which undergoes a red-shift and reduction of GP.

The spatial resolution of the measurement, and the region from which fluorescence is collected, was controlled in this example by adjusting the size of an aperture 166 located in the confocal microscope image plane.

For the first five seconds of the experiment, the trapping laser beam was turned off, and the vesicle fluorescence excited in the UV range and continuously monitored. The GP was measured to have a constant value of 0.40, corresponding to an initial setpoint temperature of 30.5° C., just slightly below $T_t$.

When the cw trapping laser (170 mW) was turned on, the vesicle was quickly trapped, and there was a dramatic decrease in the value of GP to approximately 0.03, indicating a quick response and temperature increase of 2.4° C.

For the next ten seconds, as long as the trapping beam was held on and used to confine the vesicle, both the GP and sample temperature were held constant, and quasi-thermal equilibrium conditions were established.

However, once the trapping beam was shut off, the vesicle GP was observed to return to its original value of 0.40, and the initial sample temperature was re-established. These results indicate that the phase transition process measured in the vesicle is reversible. The rise and fall times for the thermal switching process are estimated to be approximately 10 ms, respectively, and are governed by the rate of heat conduction away from the locally heated region.

These results also indicate that the confinement by an IR trapping beam results in sample heating. When the trapping power is increased above 170 mW, a substantially larger change in GP, and hence in temperature, was observed. For example, at 255 mW, the liposome temperature was increased nearly 3.7° C.

Figure 4:
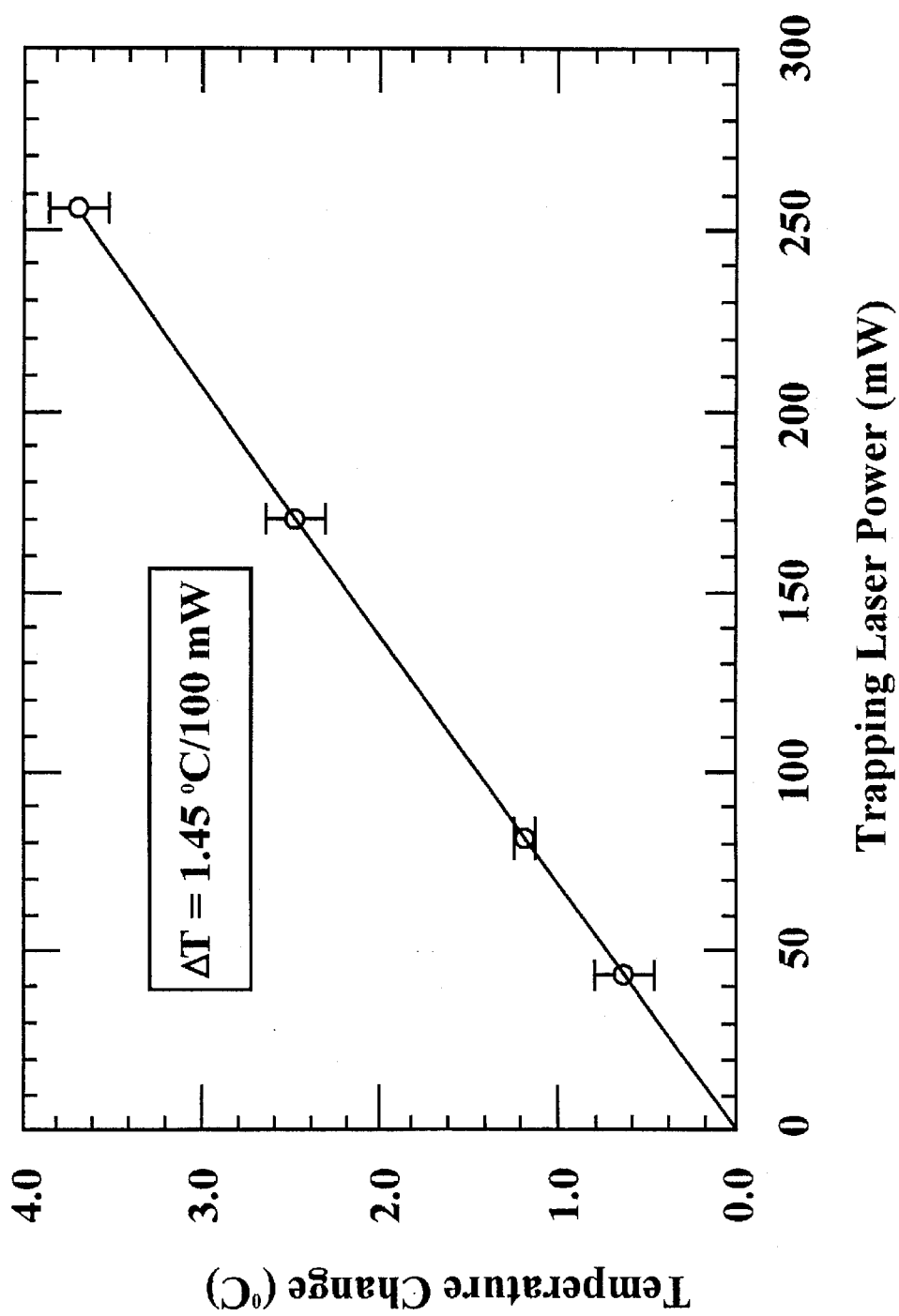
FIG. 4 is a graph of temperature change induced in an exemplary phospholipid vesicle according to the present invention described in Example 2 below, in response to heating from exposure to a trapping laser.

FIG. 4 illustrates the results of such a procedure, as measured experimentally. The initial temperature of the sensor was 30.5° C., and the sensor 10 changed its fluorescent emission wavelength with exposure to the laser. The relationship between the sample temperature was determined experimentally to increase linearly with prolonged exposure to the laser radiation for the region close to $T_t$ of the sensor 10. Hence, this temperature change may be characterized by the slope of the sample temperature/applied laser power curve of FIG. 4, representing the ratio of the change in sample temperature, $\Delta T$, to applied laser power P. This slope was experimentally measured to be approximately 1.45±0.15° C./100 mW for the conditions and sensor 10 described above.

Hence, by converting the change in GP data into change in temperature values, the relationship illustrated in FIG. 4 is obtained. This relationship closely correlates to theoretical values obtained by heat transfer theory. This supports the validity of the temperature readings obtained by the sensor.

This example demonstrates the value of the present invention, as it provides a mechanism to measure such temperature changes. Such data could not readily be obtained by other experimental techniques.

EXAMPLE 3

A similar experiment to that illustrated in Example 2 was performed with vesicles with a DPPC membrane doped with Laurdan™ ($T_t$=42° C.) and an approximate size of 10 µm. These were irradiated by a Nd:YAG laser operating at 1.064 µm and focused to a spot size of approximately 1 µm. At this wavelength, sample heating is primarily due to water absorption within the membrane region.

To quantify the change in sample temperature as a result of heating by laser exposure, the vesicle temperature was initially set to 37° C., a value below $T_t$ for this choice of cell membrane, with the laser turned off.

Next, the sample was exposed to the laser radiation, and the fluorescence continuously monitored. Fluorescence photobleaching was avoided by gating the ultraviolet excitation beam used in the fluorescence measurements.

Figure 5:
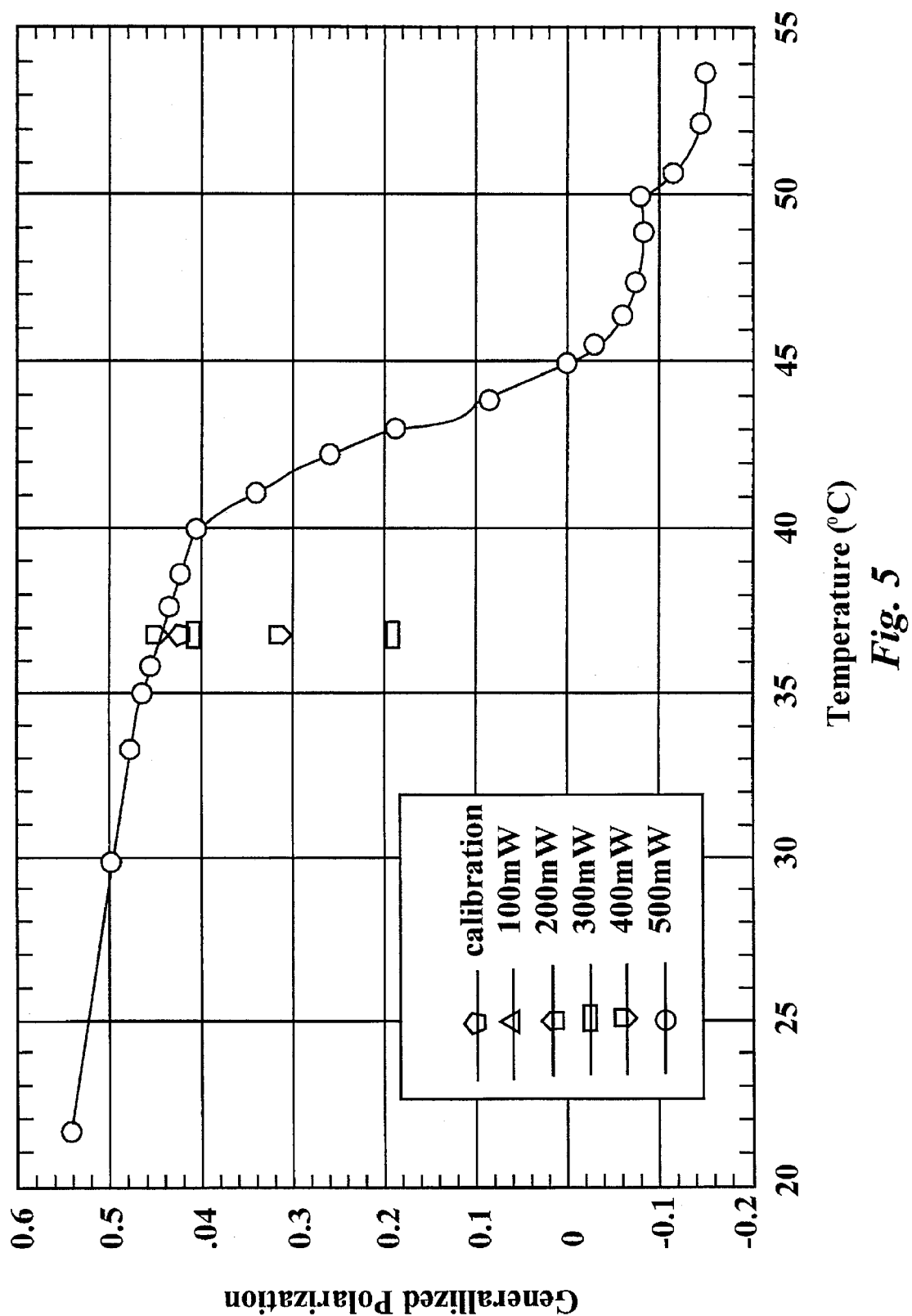
FIG. 5 is a graph of temperature change plotted against Generalized Polarization for an exemplary vesicle according to Example 3 described below.

A shift in the fluorescence emission wavelength was then observed, resulting in a change in GP and new effective temperature. The plot of GP as a function of temperature measured is shown in FIG. 5. The ratio of the change in sample temperature, $\Delta T$, to applied laser power P was experimentally measured to be approximately 1.1° C./100 mW for this example.

Again, this example demonstrated that for temperatures close to $T_t$, there was a linear relationship between incident laser power and sample temperature.

EXAMPLE 4

Another test was performed, like Example 2, except that instead of the biosensor described above, living cells were used. In particular, chinese hamster ovary (CHO) cells were doped with Laurdan™.

A 4×10-4M solution of Laurdan™ in ethanol was added to the cell-containing medium such that the ethanol concentration was 3%. The medium itself consisted of GIBCO's minimal essential medium, supplemented with 10%/vol. fetal bovine serum, 2 mM L-glutamine, 100 units/ml penicillin, and 100 mg/ml streptomycin. The cells were first incubated at 37° C. for 35 minutes, then treated with 0.25% trypsin to cause the cells to detach, followed by a fresh medium rinse to deactivate the enzyme. The medium with detached cells was placed in a culture tube and centrifuged for 5 minutes at 1000 g. The supernatent was removed and the cell pellets were then resuspended in PBGC. This procedure resulted in dye-tagged CHO cells, having typical sizes of 8–15 µm in diameter. In the present example, two CHO cells of 10 µm diameter were measured.

The experiments demonstrated that while the living cells have a more heterogeneous membrane structure and exhibit more subtle phase transition features, as assayed by the Laurdan™ probe and GP measurements, the Laurdan™ is still sensitive to temperature and local environment of the membrane.

More specifically, the measurements showed an almost monotonic decrease with increasing temperature of approximately $\Delta GP/\Delta T = 9.0 \pm 2.0 \times 10-3/°C$. In comparison to the vesicles described above, CHO cells do not display a distinct phase transition feature at a given temperature in the GP curve. They are less sensitive to small temperature variations, but display a much larger linear dynamic range. As a result, they may be used to measure the extent of localized heating over a much greater temperature range.

This observed difference in behavior is the cellular plasma membranes. This is also suggested by some variation between the two measured cells and possible observed bilayer phase transition data measured at several temperatures. In addition, the differences may be the result of nonuniform incorporation of Laurdan™ dye into the CHO membrane.

Hence, such a sensor as described above is ideally adapted for use in-situ. The sensor enables the user to accurately perform microthermometry of biological systems. The sensor is made of organic materials similar to those of the biological system's cell nuclei and membranes, and is micron-sized. Therefore, it can be embedded within biological systems such as cells, or transported within the body, to facilitate non-invasive and non-destructive site-specific microthermometric measurements. The sensor may be transported and manipulated using radiation pressure forces of focused laser beams, or even coupled, as a transducer element, to an optical fiber tip for remote sensing of temperature.

Given the high spatial resolution of the sensor, it should also be possible to perform metabolic imaging and thermal mapping of cell and tissue systems at the submicron level. This would assist in assessing, optically and in real-time, the effects of exposure to highly focused laser beams on tissues during diagnostic and therapeutic treatment.

Further, such a sensor will allow for study of the effects upon tissues of therapeutic treatment techniques such as the use of lasers, and even of "optical tweezers" and other procedures thought to be benign.

To those skilled in the art to which the invention disclosed herein relates, many changes in construction and method, and widely differing embodiments and applications of the invention, will suggest themselves without departing from the spirit and scope of the invention. The disclosures and the descriptions herein are purely illustrative and are not intended to be in any sense limiting. The actual scope of the invention described herein is only limited by the scope of the appended claims.

What is claimed is:

1. A method for high resolution in-situ measurement of temperature at a location within an aqueous biological system comprising:

(a) selecting a vesicle comprising a phospholipid membrane impregnated with an environmentally sensitive fluorescent dye, said membrane having a transition temperature at which said membrane undergoes a phase transition between gel and liquid-crystalline states chosen to be in predetermined relationship to the anticipated temperature range of the system to be measured, said membrane having a known relationship between generalized polarization and temperature, generalized polarization being the ratio $(IG-IL)/(IG+IL)$ of the difference to the sums of the intensities measured at the maximum emission wavelengths in the gel (IG) and liquid-crystalline (IL) phases;

(b) introducing said vesicle into the biological system to be measured;

(c) manipulating said vesicle to the location where temperature is to be measured;

(d) optically measuring the generalized polarization of said vesicle; and (e) calculating a value for the temperature of said system from said generalized polarization measured and said known relationship between temperature and generalized polarization for said membrane of said vesicle.

2. The method of claim 1 further comprising:

(f) obtaining a calibration generalized polarization for said vesicle by measuring the generalized polarization of said vesicle at a predetermined temperature prior to introduction of said vesicle into the biological system to be measured;

wherein said calibration generalized polarization is utilized in said step (e) by modifying said known relationship between temperature and generalized polarization for said membrane of said vesicle.

3. The method of claim 1 wherein said manipulating of said vesicle comprises use of an optical laser trap consisting of a highly focused laser beam that creates optical tweezers.

4. The method of claim 1 wherein said vesicle is attached to an optical fiber and said step of manipulation of said vesicle comprises manipulation of said optical fiber.

5. The method of claim 4 wherein said optical fiber is disposed in a catheter.

6. The method of claim 1 wherein said environmentally sensitive fluorescent dye comprises 6-dodecanoyl-2-dimethylaminonaphthalene (Laurdan™).

7. A method for measuring a temperature local to a living cell having a cell membrane, said method comprising:

(a) doping said cell membrane of said cell with a fluorescent dye, said cell membrane having a known transition temperature at which said membrane undergoes a phase transition between a gel phase and a liquid-crystalline phase, the gel phase and the liquid-crystalline phase each having a maximum emission wavelength at which its intensity is at a maximum and an associated intensity at the maximum emission wavelength, the intensities referred to as IG and IL for the gel phase and liquid-crystalline phase, respectively, said cell membrane having a known relationship between generalized polarization and temperature, generalized polarization being defined as the ratio $(IG-IL)/(IG+IL)$ of the difference of the intensities IG and IL to the sums of the intensities IG and IL;

(b) optically measuring an observed generalized polarization of said cell membrane; and (c) calculating a value for the temperature of said cell membrane from said observed generalized polarization and said known relationship between temperature and generalized polarization for said membrane of said cell.

8. The method of claim 7 wherein said environmentally sensitive fluorescent dye comprises 6-dodecanoyl-2-dimethylaminonaphthalene (Laurdan™).

* * * * *